United States Patent
Hagerman et al.

(10) Patent No.: US 7,855,053 B2
(45) Date of Patent: Dec. 21, 2010

(54) METHODS FOR DETECTING THE PRESENCE OF EXPANDED CGG REPEATS IN THE FMR1 GENE 5' UNTRANSLATED REGION

(75) Inventors: Paul J. Hagerman, Davis, CA (US); Flora Tassone, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/779,873

(22) Filed: Jul. 18, 2007

(65) Prior Publication Data

US 2008/0113355 A1 May 15, 2008

Related U.S. Application Data

(60) Provisional application No. 60/832,024, filed on Jul. 19, 2006.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search .............. 435/6, 435/91.2; 536/24.33
See application file for complete search history.

(56) References Cited

U.S. PATENT DOCUMENTS 6,107,025 A * 8/2000 Caskey et al. ................. 435/6
7,022,486 B2 4/2006 Campbell

OTHER PUBLICATIONS

Strelnikov, V. et al. A simple multiplex FRAXA, FRAXE, and FRAXF PCR assay convenient for wide screening programs. Human Mutation, vol. 13, pp. 166-169, 1999.*

Strelnikov, V., et al., "A simple multiplex FRAXA, FRAXE, and FRAXF PCR assay convenient for wide screening programs," 1999, *Human Mutation*, vol. 13, pp. 166-169.

Tassone et al., "A Rapid Polymerase Chain Reaction-Based Screening Method for Identification of All Expanded Alleles of the Fragile X (*FMR1*) Gene in Newborn and High-Risk Populations," Jan. 2008, Journal of Molecular Diagnosis, vol. 10, No. 1, pp. 43-49.

Warner et al., "A General Method for the Detection of Large CAG Repeat Expansions by Fluorescent PCR," 1996, J. Med. Genet., Dec. 1996; 33: 1022-1026.

* cited by examiner

*Primary Examiner*—Suryaprabha Chunduru
(74) *Attorney, Agent, or Firm*—Townsend and Townsend and Crew LLP

(57) ABSTRACT

The invention provides improved methods for detecting the presence of expanded CGG repeats in the fragile X mental retardation 1 (FMR1) gene and for quantifying the amount of protein produced by the gene.

11 Claims, 2 Drawing Sheets

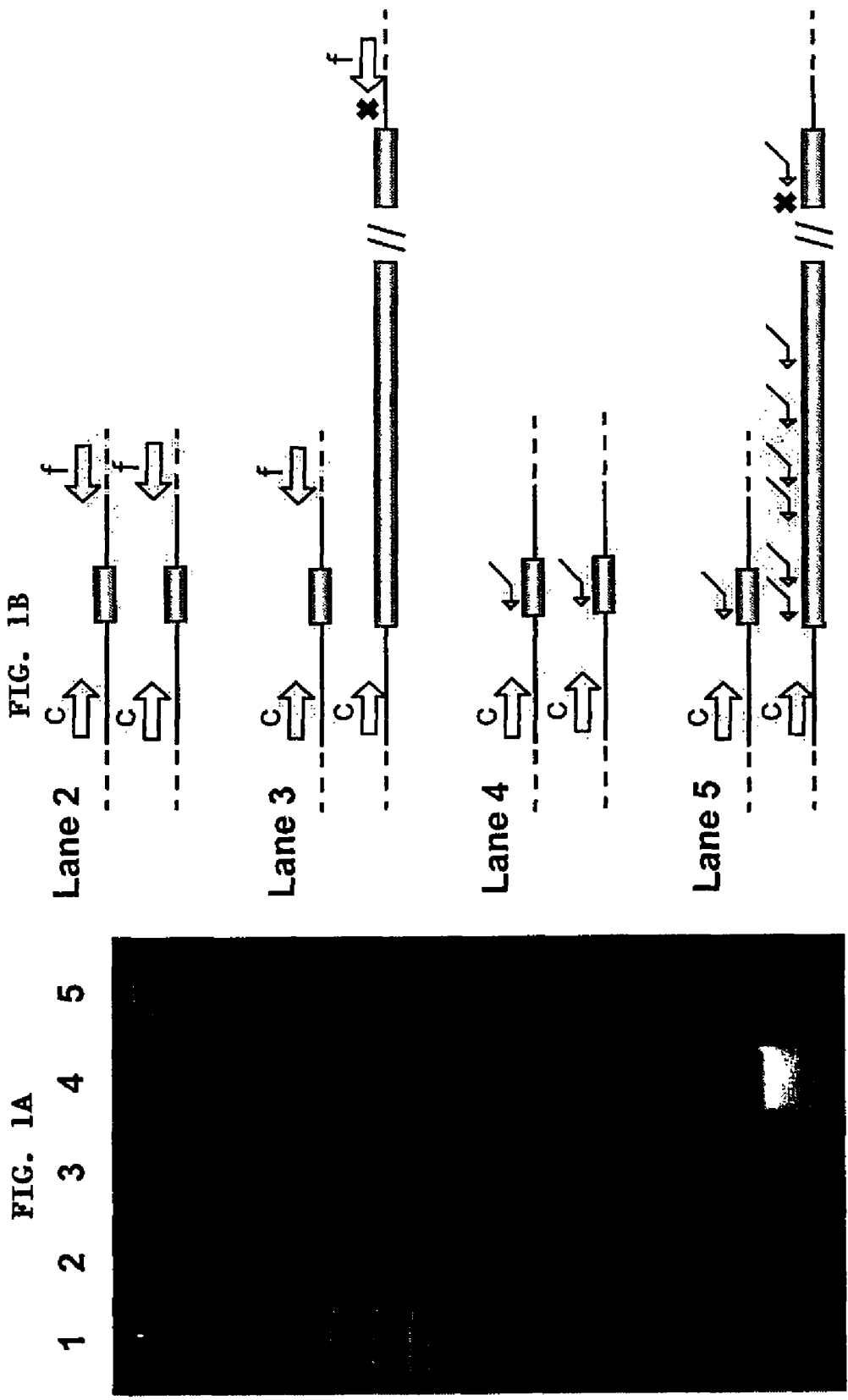

Figure 2

```
13681  cagcggggccg ggggttcggc ctcagtcagg cgctcagctc cgtttcggtt tcacttccgg
13741  tggagggccg cctctgagcg ggcggcgggc cgacggcgag cgcgggcggc ggcggtgacg
13801  gaggcgccgc tgccaggggg cgtgcggcag cgcgggcgcg gcgggcgggc cggcgggcggc
13861  ggaggcgggcg gcggcgggcg cggcgggcgg ggctgggcct cgagcgcccg cagcccacct
13921  ctcggggcg ggctcccggc gctagcaggg ctgaagagaa gATGgaggag ctggtggtgg
13981  aagtgcgggg ctccaatggc gctttctaca aggtacttgg ctctagggca ggcccatct
```

METHODS FOR DETECTING THE PRESENCE OF EXPANDED CGG REPEATS IN THE FMR1 GENE 5' UNTRANSLATED REGION

CROSS-REFERENCES TO RELATED APPLICATIONS

This disclosure claims the benefit of U.S. Provisional Application 60/832,024, filed Jul. 19, 2006, the contents of which are hereby incorporated by reference.

STATEMENT AS TO RIGHTS TO INVENTIONS MADE UNDER FEDERALLY SPONSORED RESEARCH AND DEVELOPMENT

This invention was made with government support under Grant No. AG024488, awarded by the National Institutes on Aging, and Grant No. HD40661, awarded by the National Institute of Child Health and Human Development. The government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Fragile X syndrome ("FrX" or "FXS") is the most common inherited form of mental retardation in males, with reported incidences of 1 in 4000 in males and 1 in 8000 in females. FXS is caused by the absence or a reduced level of the protein encoded by the fragile X mental retardation ("FMR1") gene; the gene is generally turned off when a CGG DNA repeat with a non-coding portion of the gene is expanded to greater than 200 CGG repeats. The FMR1 gene is on the X chromosome, and is located at Xq27.3. The gene has a length of 38 kb and encodes a 4.4 kb transcript with 17 exons. (O'Donnell and Warren, Annu Rev Neurosci 25:31538 (2002). The gene sequence is publicly available under accession number L29074 in the National Center for Biotechnology Information (NCBI) "Entrez Nucleotide" database via the NCBI website. The fact that females have two alleles for the gene (one on each X chromosome) while males have only one (since they carry one X chromosome and one Y chromosome) accounts for the difference in incidence and severity between the male and female populations.

Fragile X syndrome results from the presence of too many copies of the trinucleotide CGG repeat in the 5' untranslated region ("UTR") of the FMR1 gene. Most people carry between about 6 and 40 trinucleotide repeats. In persons with over 200 trinucleotide repeats (known as a "full mutation"), the repeats are generally hypermethylated, and the gene is silenced.

Persons are considered to have a premutation expansion of the FMR1 gene if they have between about 55 to 200 trinucleotide repeats, and to have a full mutation when they have more than 200 repeats. Males and some females with either premutation or full mutation forms of the gene (alleles) are considered to be carriers. Individuals with permutation alleles are at increased risk for developing fragile X-related disorders as adults. Approximately 1 in 5 adult women premutation carriers will experience premature ovarian failure ("POF") and approximately 40% of men over 50 years of age, and a smaller number of women, who are identified through known fragile x families, will develop the neurodegenerative disorder, fragile X-associated tremor/ataxia syndrome (FXTAS) (Jacquemont et al., Lancet Neurol 6:45 (2007)). Both males and females with full mutation forms of the FMR1 gene generally develop features of the child-onset disorder, FXS, although females are usually less affected than are men since they typically have a second allele of the gene without the mutation, which provides some expression of the protein encoded by the FMR1 gene.

Better identification of carriers and earlier identification of infants with Fragile X syndrome could be accomplished by screening of both the general population and of newborns, in particular, for expanded alleles of the gene. (Bailey, D. B. Jr. et al., *Ment Retard Dev Disabil Res Rev* 10:3-10 (2004)). Early intervention in infants and toddlers with developmental delay (intellectual disability), and associated behavioral problems (e.g., autism), focusing on language, motor, social and cognitive development, results in improved developmental and behavioral outcomes. (See, e.g., Guralnick, M. J. *Am J Ment Retard* 102:319-45 (1998); Shonkoff, J. P. et al., *Handbook of Early Childhood Intervention*. New York: Cambridge University Press, (2000); Bailey, D. B. Jr. et al., *Ment Retard Dev Disabil Res Rev* 10:3-10 (2004)).

No prospective, controlled studies have been carried out, however, that specifically examine the efficacy of early intervention in fragile X syndrome. Early diagnosis would not only permit the study of intervention in such cases, but would allow families to obtain genetic counseling at a time that will make a difference for subsequent pregnancies (Bailey, D. B. Jr. et al., *Ment Retard Dev Disabil Res Rev* 10:3-10 (2004)). In addition, early diagnosis will become even more important as newer psychopharmacological treatments are developed specifically for FXS (e.g., mGluR5 receptor antagonists; Hagerman, R. J. "*Fragile X Syndrome: Diagnosis, Treatment and Research*" Baltimore: The Johns Hopkins University Press" 287-338 (2002); Berry-Kravis, E. et al., *Ment Retard Dev Disabil Res Rev* 10:42-8 (2004)).

The need for detecting carriers of premutation alleles is increased by recent findings that premutation alleles in females have been found to be associated with premature ovarian failure (Allingham-Hawkins, D. J. et al., Am J Med Genet 83:322-5 (1999); Sullivan, A. K. et al., Hum Reprod 20: 402-12. Epub 2004 (Dec. 17, 2005)). Moreover, a second form of clinical involvement has recently been identified among older male carriers of premutation (FMR1) alleles (Hagerman, R. J. et al., X. Neurology 57:127-30 (2001)), consisting of progressive intention tremor, gait ataxia, Parkinsonism, and autonomic dysfunction; this disorder has been designated "fragile X-associated tremor/ataxia syndrome" (FXTAS). An effective screening tool would reduce the number of missed or incorrect diagnoses for both POF and FXTAS.

It is estimated that at least one-third of all adult male premutation carriers over 50 years of age, who are ascertained through known fragile X families, will develop symptoms of FXTAS, and the penetrance appears to increase with age (Jacquemont, S. et al., JAMA, 291:460-69 (2004)). Given the carrier frequency among males of ~1/800 (Dombrowski, C. et al., Hum Mol Genet 11:371-8 (2002)), FXTAS appears to be one of the more common single-gene forms of tremor and ataxia among older adult males in the general population.

An effective screening tool for expanded alleles of the FMR1 gene must satisfy several tests: it must be able to reliably detect and size expanded alleles at least through the upper portion of the premutation range; it must be rapid in both primary detection and secondary analysis phases and identify all alleles in the full mutation range for both males and females; it must be able to unambiguously distinguish between females who are homozygous for normal FMR1 alleles (single normal band following polymerase chain reaction ("PCR"); ~40% of all females) and females with one normal allele and a second, full mutation allele that does not PCR amplify (single normal band, apparent homozygote); this third test has been the greatest impediment to high-throughput screening. Finally, the test should be inexpensive enough for large scale screening.

A number of approaches were considered in trying to develop a screening tool that meets the tests noted above. Strategies considered included fluor-labeled, PCR-based fragment analysis, and Long PCR methods based on bisulfite modification. For example, ("automated") fluorescent probe-based fragment analysis currently fails all the tests. The method cannot reliably detect premutation alleles throughout the premutation range, particularly in females, due to the rapidly diminishing signal strength of the expanded allele with increasing CGG repeat number; this latter issue requires significant operator involvement for the interpretation of each scan, thus dramatically reducing the throughput of the method. Moreover, the method is too expensive, due to the costs associated with capillary matrix, fluorescent reagents (e.g., primers), and instrument service and overhead.

Genotyping analysis is estimated to cost $15-20 per sample on a thousand sample basis. The method does not provide consistent, positive reads throughout the premutation range, particularly for DNA samples from female carriers. Furthermore, the method requires substantial time for operation and interpretation. Finally, the method does not reliably distinguish between normal homozygous females and the presence of a very large (non-PCR amplifiable) full mutation allele. Therefore, while the fragment analysis approach holds great potential for rapid, automated screening, the technology is not currently sufficiently developed to be used as a screening/testing tool.

PCR approaches based on bisulfite modification of the CGG repeat sequence (conversion of the unmethylated C nucleotides to U nucleotides) (Clark, S. J. et al., Nucleic Acids Res 22:2990-7 (1994)) hold promise for subsequent long PCR amplification, since the bisulfite-modified DNA is both lower in CG-content and of lower sequence symmetry (base pair changes within the CGG repeat element). However, the bisulfite treatment does not reliably preserve sufficient DNA for PCR from small DNA samples, such as those obtained from blood spots, due to the well-known degradation of DNA during the bisulfite conversion process (Grunau, C. et al., Nucleic Acids Res 29:E65-5 (2001)). Thus, whereas some samples can be genotyped using this approach, the method can fail unpredictably due to sample degradation during the bisulfite treatment. This method also requires additional steps in the screening process, including time and additional steps for bisulfite conversion of DNA. Approximately 6 hours are required for a complete conversion, somewhat less time if only partial conversion is required, which adds to the cost through operator time. Finally, it is very important for a successful and reliable analysis that high-quality DNA is used, which is the major pitfall of the bisulfate approach.

Thus, the ability to screen for persons with large numbers of trinucleotide repeats in the FMR1 gene is of considerable importance. The present invention fills these and other needs.

BRIEF DESCRIPTION OF THE DRAWINGS

FIGS. 1A-1B. FIG. 1A. Photo of a gel showing secondary screening method by PCR to resolve apparent homozygosity in females. The approach uses a combination of betaine and a chimeric (CGG-targeted) PCR primer that primes randomly, but with a size bias for amplification of smaller expansions, within the CGG repeat. FIG. 1B shows a schematic of the binding of primers to produce the results shown in the lanes of the gel. The PCR of normal alleles using the art standard "c" and "f" primers is shown in lane 2 of the gel (FIG. 1A) and in the schematic labeled lane 2 of FIG. 1B. PCR of normal alleles using the "c" primer (shown as an open arrow in FIG. 1B) and the chimeric primer (shown as a line arrow in FIG. 1B) results in only small PCR products, as shown in lane 4 of the gel, FIG. 1A, and in the schematic labeled as lane 4 in FIG. 1B. In contrast, PCR of large alleles using the "c" primer and the chimeric primer results in an extensive smear, as shown in lane 5 of the gel (FIG. 1A) and the schematic labeled "Lane 5" in FIG. 1B, reflecting priming within the extended CGG repeat. For full mutation alleles, priming by the standard downstream primer (primer "f") does not occur. Representation of the PCR products for each lane is given to the right of the gel image. The chimeric primer comprises a 3' $(CCG)_4$ (SEQ ID NO.:13) block for targeting and a 5' random N24 block for subsequent amplification $[N_{24}—(CCG)_4]$(SEQ ID NO:14).

FIG. 2. FIG. 2 shows the 5'UTR immediately upstream of the start of the coding region of the FMR1 gene, the start codon, and the beginning of the coding sequence (SEQ ID NO.:15). The start codon, ATG is capitalized and underlined. The CGG repeat region is in bold and underlined. Nucleotide position numbering is as set forth in the sequence set forth in the Entrez Nucleotide database under accession number L29074.

DETAILED DESCRIPTION OF THE INVENTION

The present invention provides long sought solutions to problems that have impeded screening for and analysis of expanded repeats of CGG in the 5' untranslated region ("UTR") of the FMR1 gene. These solutions permit determining whether an individual either has a premutation in the gene (indicated by 55 to up to 200 repeats) and is therefore a carrier, or has 200 or more repeats, and therefore has a full mutation in the gene. In persons with a full mutation, the repeat region becomes hypermethylated, silencing the gene. The lack of the protein, FMRP, encoded by the gene adversely affects neurological development and results in Fragile X Syndrome ("FXS").

The solutions of the invention permit large scale, cost effective screening for infants and toddlers at risk of development of FXS and for women who are carriers of a large (e.g., full mutation) allele from their normal, homozygous counterparts. Further, the solutions permit quantitating the amount of the FMRP actually expressed in individuals, thereby improving the ability to determine the degree to which a particular individual may be affected by FXS. Since early intervention and treatment of such individuals is correlated with substantially improved outcomes, the ability to diagnose early persons with FXS can reduce the burden of this disorder on the individual, on the individual's family, and on society.

A. Improvement of PCR Assaying and Detecting Females with Full Mutations.

In some embodiments, the invention provides improved methods of identifying premutation and full mutation alleles of up to ~300 CGG repeats by PCR, which can be used for high-throughput, low cost screening. Currently available techniques of PCR have not permitted identification of persons with high numbers of repeats, especially in females, and have not been adaptable for high-throughput screening. The methods of the invention permit detection of numbers of repeats well above the upper end of the premutation range, and are applicable for both males and females.

The methods can be used on small sample amounts, such as blood spots. This is an important advantage, since it permits the test to be integrated, if desired, with the routine screening of newborns already conducted in every state for phenylketonuria (PKU). PKU testing usually consists of having the child's heel pricked and a few drops of blood placed on a card and sent to a lab for determination of blood phenylalanine levels. The inventive methods allow the blood spots on the card to also be used to determine whether a boy or girl has an expanded FMR1 allele, permitting routine and large scale screening for these conditions.

Application of PCR to amplification of FMR1 genes with more than about 100 to 150 repeats of CGG has been difficult because the high CG content has made separating the strands too difficult for standard techniques. This has permitted detection of only some of the persons with permutation alleles. Further, because females have two FMR1 alleles, one on each X chromosome, attempts to amplify the CGG-containing 5' untranslated region (UTR) in females with one normal allele and one allele in which there are a high number of repeats has resulted in the amplification of the normal allele, concealing the presence of the high-repeat allele.

The methods of the invention provide a solution to both of these problems. First, the methods modify a commercially available system, the Expand Long Template PCR system (Roche Diagnostics, Mannheim, Germany) by using higher than normal concentrations of the osmolyte betaine (N,N,N-trimethylglycine). Frackman et al., Promega Notes 65:27 (1998), note that a variety of additives and agents can be included in PCR amplifications to increase yield, specificity and consistency. Their list of such agents includes dimethyl sulfoxide (DMSO), betaine, formamide, glycerol, nonionic detergents, bovine serum albumin, polyethylene glycol and tetramethylammonium chloride. DMSO is noted to be useful in disrupting base pairing, whereas betaine is noted to equalize the contribution of G-C and A-T base pairing to the stability of the DNA duplex. Id. When used with high G-C content DNA, Frackman et al. recommend the use of 1 M betaine, while others recommend the use of 1.3 M betaine with 1.3% DMSO. Studies underlying the present invention found that the use of betaine at 1.3M did not result in the ability to detect persons with 200 repeats.

Surprisingly, increasing the concentration of betaine from 1.7 M to about 2.2 M permitted detecting CGG repeats at numbers ranging from normal (4-54) throughout the premutation range in both males and females. The PCR products could be directly visualized on agarose gel after ethidium bromide staining; subsequently, the size of the alleles can be more precisely sized on acrylamide gels or by fragment analysis, if required.

While this by itself is a useful and important advance, it does not also solve the problem of how to provide low-cost, high-throughput screening for heterozygous females. One of skill will appreciate that, for males, one will see only one band upon PCR, since males only have one allele. Females, in contrast, should show two bands, one for each allele. The problem arises from the fact that, in 40% of females, only one band will be visible. This can arise, however, from either of two very different possibilities, which are best explained by presenting three scenarios. In the first scenario, the female has two normal alleles, each of which having approximately the same number of repeats. In this scenario, only one band will be visible on the gel due to indistinguishability of the two alleles. In the second scenario, the female has one allele with a normal number (e.g., 30) of repeats, and a premutation expansion (e.g., 150 repeats) for the second allele. In this scenario, two bands will be visible, one (the allele with 30 repeats) being fairly dark, and the second one being light, but visible. In the third scenario, the female has one normal allele, with 30 repeats, and one allele with a full mutation, with 400 repeats. In this scenario, only one band, for the normal allele, will be visible. PCR will not amplify the second allele.

The problem is that the first scenario describes some 40% of females, while the third scenario describes one in 3000. Thus, out of 10,000 females, 4000 will show a single band, of which 3 will have a full mutation. PCR alone does not permit distinguishing between the 3997 with two normal alleles and the 3 with a full mutation of one allele. Thus, standard PCR, even with the improvement of increasing betaine concentration does not permit rapid, high-throughput assaying for females with full mutations.

The present invention solves this problem. Surprisingly, it rests in part on the realization that one does not have to amplify the entire CGG repeat region to determine the presence of a full mutation. Rather, the present invention stems in part from the realization that a primary screening tool does not need to define the exact size of a full mutation allele, but only to signal its presence. The problem of resolving which of the 40% of females who appear homozygous have a full mutation can then be determined by defining the size of the full mutation allele with more traditional methods (e.g., Southern gels). Previous attempts to solve this problem have failed in part because of the difficulty of amplifying the full CGG repeat region.

Persons of skill are aware that the 5' UTR region of the FMR1 gene has been defined and, except for the portion that comprises the CGG repeats, is uniform among individuals (as noted in the Background, the entire FMR1 gene has been sequenced and made publicly available). Thus, the practice in the art is to amplify the 5' UTR region containing the CGG repeat region by using primers which hybridize within the 5' UTR in the sections flanking the CGG repeat region. Two widely used sets of such primers are the "c" and "f" primers (Fu Y H et al. Cell 67:1047(1991)): 5'-agccccgcacttc caccaccagctcctcca-3' (SEQ ID NO.:1) and 5'-gctcagctccgtttcggtttcacttccggt-3' (SEQ ID NO.:2), and the "1" and "3" primers employed by Brown et al., JAMA, 270:1569-75 (1993). The "1" and "3" primers are on the outsides of the regions flanking the CGG repeat region and therefore capture a larger portion of DNA, while the "c" and f primers result in a smaller amplicon and greater resolution. Neither of these sets of primers, however, can amplify the CGG repeats of a full mutation.

In the present invention, samples from females that display a single band in the normal range (that is, females who could be a homozygote or could have a normal allele and a full mutation) in a first round of screening are resolved by a second round of screening. The first round of screening can use conventional primers, such as those of Fu or Brown. Any pair of upstream/downstream primers bracketing the CGG repeat region can be used for the first round screening, and it is understood within the art that such primers are selected with respect to stability and specificity using commonly known programs for determining primers. Typically, the upstream primer will be a nucleotide sequence complementary to a portion of the 5' untranslated region of the FMR1 gene that is not within the CGG repeat region. Since the Fu and Brown primers are readily available and work well, however, it is convenient to use them for in the first round screening.

In the second round, as usual, two primers are used for the PCR reaction. As for the first round screening, one primer is a nucleotide sequence complementary to a portion of the 5' untranslated region of the FMR1 gene that is not within the CGG repeat region. Conveniently, the first primer can be one of the standard primers used in PCR of the CGG region, such as the "c" primer of Fu or the "1" primer of Brown. The sequence of the 5' UTR upstream (that is, 5') of the CGG repeat is known, however, and the person of skill can readily design any number of additional, alternative 5' primers using standard techniques. General guidelines for designing efficient and specific primers are well known in the art and are taught in, for example, Innis, et al., eds., PCR PROTOCOLS: A GUIDE TO METHODS AND APPLICATIONS, 1990 (Academic Press, San Diego Calif.), and Dieffenbach and Dveksler, PCR PRIMER A LABORATORY MANUAL, 2003 (Cold Spring Harbor Laboratory Press, Cold Spring Harbor, N.Y.). In some preferred embodiments, the 5' primer is the "c" primer or the "1" primer, with the c primer being more preferred.

In the sequence set forth for the FMR1 gene in the Entrez Nucleotide database, under accession no. L29074, the ATG start codon, which defines the downstream end of the non-coding 5'UTR, commences at position 13962. The CGG repeat region starts at position 13833 and ends at position 13962, as shown in FIG. 2. Persons of skill will appreciate that the deposited sequence is that of a person with a normal allele. The number of repeats in this region is highly variable within the human population, and pre-mutation or full mutation alleles will have more CGG repeats than shown in FIG. 2. The nucleotides on either side of the CGG repeat region, however, will be the same. SEQ ID NO.: 12 sets forth the sequence of the gene upstream of the start codon, as set forth under accession number L29074, as well as the start codon (commencing with the "a" at position 13962) and a portion of the beginning of the coding sequence as set forth in FIG. 2. As noted, the CGG repeat region commences at position 13833. Therefore, the first primer is designed to hybridize to portions of SEQ ID NO.:12 that are 5' of position 13833.

As persons of skill will appreciate, the 5'UTR of a gene is that portion of the gene that is the template of the untranslated part of the RNA produced by the gene. With respect to the FMR1 gene, the 5'UTR is considered to commence at approximately nucleotide 13701. For amplifying a portion of the gene, the location of the 5'UTR is relatively unimportant since primers can be selected to amplify kilobases of genome. Better resolution of the area of interest, however, is achieved by amplifying smaller sequences, and it is thus preferable to select a 5' primer that hybridizes relatively close to the CGG repeat region. Thus, the primer is preferably selected to hybridize to a region 500 or fewer nucleotides 5' of position 13833, more preferably 400 or fewer nucleotides 5' of position 13833, more preferably 300 or fewer nucleotides 5' of position 13833, still more preferably 200 or fewer nucleotides 5' of position 13833, even more preferably 150 or fewer nucleotides 5' of position 13833, and most preferably 100 or fewer nucleotides 5' of position 13833. Persons of skill will also be aware that the primer is preferably selected to hybridize to a portion of the genomic DNA that has 40-60% A or T nucleotides so that the annealing of the primer to the genomic DNA is not more stable than desirable for ready separation of the strands during the amplification cycles. Such primers can include, for example, a 20-mer complementary to positions 13391 to 13409 of SEQ ID NO.:12, and a 20-mer complementary to positions 13661 to 13680 of SEQ ID NO.:12. The "c" and "1" target the region defined by the sequence lying between 13701 and 13833. The "f" and "2" primers target sequence that lies downstream of 13892 in SEQ ID NO.:12; such sequence can include UTR sequence but can also include coding sequence downstream of the ATG.

Unlike the case for the first round PCR, the second primer comprises CCG repeats that "sit down" randomly within the CGG repeat region instead of in the flanking region. The second primer may vary in the number of CCG repeats that it possesses, with numbers between 3 and 9 being preferred for ease of synthesis, 4-8 repeats being more preferred, 4, 5, 6 or 7 repeats being still more preferred, 4, 5, or 6 repeats being more preferred yet, and 4 or 5 repeats being especially preferred. In some embodiments, four repeats are particularly preferred. Rather than providing a single band indicative of a full mutation, which has been the goal of previous, but unsuccessful methods, when applied to a sample from a person having an allele with a full mutation, the inventive method results in a broad smear as the result of amplicons of multiple different lengths. The smear is indicative of the presence of a full mutation. CGG repeats were used in initial studies and can be used; however, better results were obtained with CCG repeats as the second primer, and are preferred. Use of either CCG repeats or CGG repeats are preferred to any combination of CGG and CCG repeats in the same primer.

The invention also provides a solution to an additional concern. The second primer can simply be a series of CCG repeats (complementary to the CGG repeats in the strand amplified by the "c", "1", or equivalent primer) as described above. Because a CCG primer sits randomly in the repeat area, over multiple cycles of amplification, the amplicons tend to become smaller in size, since random priming within the CGG repeat-containing amplicons will always produce shorter products for a given round than the amplicons produced by the preceding round. While a pure $(CCG)_n$ second primer is useful, it would be preferable to have a second primer that results in maintaining the size of the amplicons after multiple cycles of amplification.

The invention solves this problem as well. In preferred embodiments, the second primer is a "chimeric" primer, so-called because it includes both a 3' portion that is composed of CCG repeats as described in the preceding paragraph, contiguous to a 5' end that has a nucleotide sequence that is random. After one or more rounds of amplication, however, the resulting amplicons contain a sequence complementary to the 5' end of the chimeric primer. This sequence on the amplicons is perfectly complementary to the sequence on the 5' end of the chimeric primer and, without wishing to be bound by theory, the hybridization of these perfectly complementary sequences is energetically favored. Thus, after the first few rounds of amplification, the size distribution of the amplicons is "locked in."

Within the constraints noted below, the sequence on the 5' end of the chimeric primer can be a varied sequence of approximately 12-60 nucleotides, with 12-30 being preferred and 21-27 being more preferred. A 24 nucleotide sequence is particularly preferred, and for convenience may be referred to herein as "N24". In the first cycle of amplification, the chimeric primer "sits" on the CGG repeat region of the FMR1 gene by hybridization of the CCG repeats of the primer to the CGG repeats of the 5'UTR of the gene. Preferably, regardless of the length of the particular sequence chosen for the 5' end of the chimeric primer, A or T nucleotides constitute between about 30% to 70%, or more preferably 40-60%, of the total number (for example, 10 A or T nucleotides out of 24 total would constitute 42% AT of the 5' end of the primer). Further, repeats of CCG are preferably avoided in the 5' end of the chimeric primer to avoid having it compete with the 3' end in sitting down in the CGG repeat region.

Surprisingly, the chimeric primers of the invention are effective, whereas a pure CCG primer with 10 CCG repeats was not effective. Without wishing to be bound by theory, it is believed that primers with 10 or more repeats of CCG or CGG may form undesirable secondary structures that could interfere with amplification.

In a preferred embodiment, the second, chimeric primer is a "(CCG)$_4$" with a N24 5' end, such as: 5'-AGC GTC TAC TGT CTC GGC ACT TGC CCGCCGCCGCCG-3' (SEQ ID NO.:4), where the underlined portion will sit down randomly within the CGG repeat region in the FMR1 5'UTR. Since these embodiments of the second primer have a 24 nucleotide 5' end, these embodiments of the chimeric primer can also be referred to as "N24(CCG)$_4$". Other examples of N24(CCG)$_4$ chimeric primers include 5'-GAC CTG TAT TGG GTC ACG TCA GTC CCGCCGCCGCCG-3' (SEQ ID NO.:5), 5'-AGC GCT ATC TCT TCC AGA GCT TTC CCGCCGCCGCCG-3' (SEQ ID NO.:6), and 5'-GCT CGC TAC TGC TTC CGG TAC CGT CCGCCGCCGCCG-3' (SEQ ID NO.:7). As described above, any of these chimeric primers could be varied by, for example, omitting the first three nucleotides of the 5' end to form an "N21" chimeric primer, such as 5'-GTC TAC TGT CTC GGC ACT TGC CCGCCGCCGCCG-3' (SEQ ID NO.:8), or by having three additional nucleotides, to form an "N27" chimeric primer, such as a different number of CCG repeats, 5'-ATT GCT CGC TAC TGC TTC CGG TAC CGT CCGCCGCCGCCG-3' (SEQ ID NO.:9), or by varying the number of CCG repeats, to provide for example 3 (for example, 5'-AGC GTC TAC TGT CTC GGC ACT TGC CCGCCGCCG-3' (SEQ ID NO.:10), or six (for example, 5'-AGC GTC TAC TGT CTC GGC ACT TGC CCGCCGCCGCCGCCGCCG-3' (SEQ ID NO.:11). The practitioner will appreciate that numerous additional chimeric primers can be designed following the teachings set forth herein.

PCR using a first primer in the 5' UTR region preceding the CGG repeat region (such as the "c" or "1" primers) and a second primer of the invention gives rise to a large smear on the analytical agarose or acrylamine gel (or any other suitable analytical sizing medium or column), either manual or automated, that indicates the presence of expanded alleles. An example is shown in FIG. 1A, lane 5. Since this second screen is only conducted on samples from females who have had a single band (which indicates that they do not have an allele with repeats that would fall into the premutation range), the smear indicates that the male or female has a full mutation. A sample from an individual without an expanded allele will not create a large smear. In this manner, normal alleles of the same or nearly the same size in females can be readily distinguished from carriers of expanded alleles.

While simple, the presence of the smear signals the presence of a second, large allele, whereas the absence of the smear confirms true homozygosity. This method is extremely rapid, and is amenable to use in automated procedures that allow thousands of samples to be screened per day. To enhance its use in automated procedures, the method can further be extended to incorporate the use of fluorescent primers and capillary or gel-based automated scanning procedures. Alternatively, the primers may optionally be labeled at their 5' ends with, for example, radionuclides. Labeling is, however, not necessary for the practice of the invention.

The present invention modifies the basic PCR protocol to allow direct reads of unmodified DNA samples, for both males and females, throughout the premutation range. Furthermore, the method allows direct analysis by ethidium staining on gels, since no modified nucleotides are required for PCR amplification through the expanded CGG repeat.

As noted, the PCR methods of the invention preferably use the modified amino acid betaine. Betaine permits PCR amplification of very GC-rich sequences, due to the destabilizing properties of the amino acid (with respect to DNA), as well as its stabilizing action on the polymerases (Baskaran, N. et al., *Genome Res* 6:633-8 (1996)). Furthermore, betaine appears to allow the PCR reaction to overcome low levels of contaminants that can co-purify with DNA (Weissensteiner, T. et al., *Biotechniques* 21:1102-8 (1996)). This is particularly important in protocols that utilize blood spots, where contaminants on the filters may interfere with PCR reactions. In studies underlying the invention, this approach has allowed PCR reactions to be run directly off of blood spots on their collection papers without any need to even perform a denaturation/separation step prior to PCR amplification.

Use of the betaine protocol of the invention has allowed consistent detection of expanded alleles throughout the premutation range for both males and females. This means that as a screening tool, all males can be typed, with no requirement for a secondary screening tool. Further, for females, all premutation carriers can be typed without the need for a secondary screening tool; that is, apparent homozygous females (single band in the normal size range) will either have two normal alleles, or will have a single normal allele with one full mutation allele. A secondary screening tool utilizes the hybrid CGG-based primer to distinguish between homozygous normal and full mutation heterozygotes/mosaic females as described.

The betaine protocol alone allows consistent detection of expanded alleles throughout the premutation range for both males and females. This means that as a screening tool, all males can be typed with no requirement for a secondary screening tool. For females, this tool identifies all premutation carriers without the need for a secondary screening tool; that is, apparent homozygous females (single band in the normal size range) will either have two normal alleles, or will have a single normal allele with one full mutation allele. A secondary screening tool will utilize the hybrid CGG-based primer to distinguish between homozygous normal and full mutation heterozygotes/mosaic females as described herein.

Although the screening protocol discussed above utilizes a DNA-based PCR amplification method, it is recognized that RNA based amplification methods are also applicable, where suitable DNA primers can be hybridized to either side of the CGG repeat, as with the embodiment described above, but with extension of the primer to include promoters for various RNA polymerases. It is known that at least some RNA polymerases can transcribe through the entire CGG repeat even for full mutation alleles, since FMR1 mRNA is produced in individuals with full mutation alleles, repeated rounds of RNA transcription/amplification will produce RNA species that reflect the sizes of the original CGG repeat element. Amplification methods which can be used in the practice of the invention include amplification methods utilizing a catalytic RNA to replicate nucleic acids, U.S. Pat. No. 4,786,600; amplification systems based on strand displacement, see Walker, et al., EP 0 497 272; and different transcription-based amplification methods. Among the latter are those of Malek, WO 91/02818; Kacian, et al., U.S. Pat. No. 5,399,491; Kacian, et al., EP 0 587 266; and McDonough, et al., EP 0 587 298.

B. Immunoassays for Fragile X

There are currently available methods for detecting the presence of fragile X mental retardation protein ("FMRP") in peripheral white blood cells. The first is an immunocytochemical staining test using a commercially available mammalian antibody from clone 1C3 directed against FMRP, in which 100 to 200 lymphocytes are identified following antibody based staining and the number of FMRP-positive cells (identified by positive staining) are counted. This method is, at best, an indirect measure of protein level, since it only scores the fraction of cells where the protein is detectable, not the level of protein in those cells. The presumption is that higher protein levels will yield more positive-staining cells. Although this trend generally holds, once most cells stain positive, no conclusions regarding protein levels can be made (ceiling effect); further, for very low protein levels, usually the case in the full mutation range, few if any cells will stain positive for FMRP (floor effect). The other disadvantage with this method is that it is time consuming. A second method, Western blot analysis, is not generally useful for detecting FMRP in non-transformed lymphocytes, due to the low protein levels in those cells, although it can be used to study transformed (lymphoblastoid) cells. A third method is hair root analysis, in which 10-20 hairs are plucked from the scalp and then subjected to the same staining procedure. This procedure can be problematic since children with FXS are often tactilely defensive and find the contact to pluck the hair difficult to tolerate. The methods are reviewed in, for example, Willemsen and Oostra, American Journal of Medical Genetics, Seminars in Medical Genetics 97(3):183-188 (2001). Since the degree of mental impairment correlates with FMRP levels in peripheral blood lymphocytes, a quantitative test would be highly useful for both diagnosis and for prognosis.

For at least a decade, groups have been trying to develop an enzyme-linked immunosorbent assay (ELISA) that would permit quantitation of the amount of FMRP. Unfortunately, no ELISA has been forthcoming. In part, this arises because of the presence of two closely related autosomal homologs, Fragile X mental retardation autosomal homolog 1 ("FXR1") and 2 ("FXR2"), that also tend to be detected by most antibodies. Further, because of the similarity between mouse and human FMRP, mouse antibodies, such as 1C3, tend to be less robust in their binding affinities to FMRP than is desirable for ELISA assays. In general, it has not been possible to develop a mammalian antibody to human FMRP due to the high sequence similarity between all (non-human) mammalian forms of the protein.

The present invention has succeeded in providing an ELISA that can be used to quantitate FMRP. A sequence from the C-terminal portion of the FMRP protein was selected since it is different from the C-terminus of the FXR1 and FXR2 proteins in an attempt to generate antibodies that could differentiate FMRP from the two homologs. Further, a non-mammalian antibody is used as the capture antibody. This combination proved successful in providing the ability to quantitate FMRP in ELISA immunoassays.

Polyclonal chicken IgY antibodies were found effective in detecting FMRP. The antibodies can be used in any immunoassay in which detection of FMRP is desired. A number of immunoassays in which the antibodies can be used are known in the art. For example, the antibodies can be labeled with enzymes, radioisotopes, or fluorescent compounds for use in enzyme immunoassays (EIA), radioimmunoassays (RIA) or fluorescence assays, can be used in assay techniques such as agglutination or turbidimetry, or detected on Western Blots.

In a preferred form, the immunoassay is an ELISA. The chicken IgY anti-FMRP antibodies are preferably used as the capture antibody. Since ELISA procedures and variations are well known in the art, they will not be described in detail herein. The following discussion sets forth the procedure for a preferred embodiment.

In brief, peripheral blood mononuclear cells (PBMCs) are isolated using Ficoll-Paque® PURE (GE Healthcare) or Vacutainer® CPT™ tubes (Becton Dickinson, Franklin Lakes, N.J.). If desired, the cells can be stored in liquid nitrogen until being assayed. The capture antibody, affinity purified chicken IgY, is coated on a well of an ELISA plate. Typically, the well is blocked with a blocking agent, such as 2% casein in phosphate buffered saline (PBS) containing 0.05% polyoxyethylene (20) sorbitan monolaurate (PBS-T). The PBMC proteins are extracted, diluted, and added to the coated and blocked well. The proteins are incubated for an appropriate time at room temperature with rocking. A standard amount of purified FMRP protein is preferably added to a duplicate well to permit quantitation of signal. The wells are then washed with PBS-T and a detecting antibody, such as mouse monoclonal anti-FMRP, with appropriate dilution (e.g., 1:10,000), is added and the mixture is incubated at room temperature for an appropriate time (e.g., 8 hours). The wells are washed with PBS-T, and a secondary antibody, such as donkey anti-mouse antibody, conjugated to a label (e.g., horseradish peroxidase) and at an appropriate dilution (e.g., 1:2000) in blocking buffer, is added to the wells and incubated. The wells are washed again and an appropriate substrate is added to detect the presence of the label.

EXAMPLES

Example 1

During the course of clinical/molecular studies of fragile X syndrome and premutation carriers, more than one-thousand samples (DNA and/or frozen PBMCs) have been archived spanning the normal, premutation, and full mutation size ranges. A sub-set of these samples, representing 980 fully characterized (PCR plus Southern) DNA samples, has the following characteristics:

| Allele[1] (# CGG repeats) | # males | # females |
|---|---|---|
| Controls (<45) | 222 | 82 |
| Gray zone (45-54) | 40 | 18 |
| Premutation (55-200) | 159 | 210 |
| Full mutation (>200) | 117 | 57 |
| Mosaics[2] | 44 (P/F); 22 MM | 6 MM |
| Total | 604 | 373 |

[1]For females, the larger allele is within the specified range.
[2]P/F, premutation/full mutation mosaic; MM, methylation mosaic.

For the female controls, 30 (52%) were apparent homozygotes (verified as normal alleles by Southern gel analysis). These samples, plus an additional 300 samples not yet fully characterized from both peripheral blood leucocytes and PBMCs, represent an important resource for the validation of the proposed screening methodology.

Example 2

Initial development of the PCR method of the invention utilized blood samples (not blood spots). Genomic DNA was isolated using the Puregene DNA Blood kit (Gentra, Inc., Minneapolis, Minn.). PCRs were performed using the "c" and "f" primers (5'-agccccgcacttccaccaccagctcctcca-3' (SEQ ID NO.:1); 5'-gctcagctccgtttcggtttcacttccggt-3' (SEQ ID NO.:2) (Fu, Y. H. et al., *Cell* 67:1047-58 (1991)) and performed using the Expand Long Template PCR System (Roche Diagnostics, Mannheim, Germany). Reaction mixtures included buffer 2

(Roche kit), 500 μM dNTPs, 0.33 μM of each primer and 100-500 ng of genomic DNA. The PCR buffer also included 2.0M betaine (B0300, Sigma-Aldrich, St. Louis, Mo.); this concentration was based on a series of PCR optimization experiments using betaine concentrations from 1.3 to 2.2 M. Previous reports recommended a concentration of 1.3 M (Baskaran, N. et al., *Genome Res* 6:633-8 (1996)). We found the cited concentration to be too low for efficient expansion of the CGG element. The expected constant region of the PCR product was 221 bp.

To establish the optimal amplification conditions, two male premutation carriers, carrying expanded alleles of 90 and 200 CGG repeats, and a control male with an allele of 20 CGG repeats were tested. Different concentration (1.3M, 1.5M, 1.7M, 2.0M and 2.2 M) were also tested. Optimal results were obtained with a range of betaine concentrations of 1.7-2.0 M.

Although alleles larger than 250 CGG repeats became progressively fainter, a PCR band was still visible in a male with ~330 CGGs (~1,300 bp). No amplification product ("amplicon") was detected for alleles >330 CGG, well above the lower bound (200 CGG repeats) of the full mutation range. It is noteworthy that carrier females with alleles of at least 160 CGGs yielded PCR products, where both the normal and expanded alleles were clearly visible as two distinct bands. The larger allele appeared proportionally weaker with increasing repeat length, but was still visible and discrete in the higher premutation range. Different molar ratios of 7-deaza-dGTP/dGTP (thought to destabilize secondary structures usually formed by CG-rich DNA sequences), in combination with the Expand Long Template PCR kit, was examined to see if this further improved results. Results with 7-deaza-dGTP were not reproducible, probably due to the weak ethidium bromide staining of DNA synthesized with this base analog. The combination of 7-deaza-dGTP and betaine did not improve amplification and, in several cases, led to a complete absence of the PCR product. Failure to detect a second band for any female with high premutation alleles (~200 CGG repeats) would convert that case to the apparent homozygote class, which would therefore be subject to the secondary screen using the hybrid CGG primer.

Example 3

For samples from males, the betaine-PCR method is capable of specifying the status (normal, gray-zone, premutation, full mutation) for all samples. Furthermore, for all categories except full mutation, the size of the allele can be determined. For apparent full mutation males (absence of a band), a secondary analysis would be performed by Southern gel to rule in/out full mutation status and to determine the size of the allele (although the latter operation is not formally part of the screen). Absence of a band would be due either to true full mutation alleles or by occasional failure of the PCR reaction. Confirmation of a full mutation allele in such cases could also be performed using the second phase of the PCR-based screening protocol, as used for females with a single band. This secondary screening method would rule out any PCR reaction failure, which could have resulted in the absence of a band for a male. Based on the expectation of one true full mutation allele per ~1/3,000-5,000 samples, one Southern gel would be needed per ~50,000 samples from males.

Example 4

For samples from females, the betaine-PCR method is capable of specifying the status of all premutation alleles based on the expectation of two bands (homozygous premutation alleles have not been described in the literature). Thus, the betaine-PCR screening procedure is capable of yielding a true estimate for prevalence of premutation carriers without the need for any additional testing. Note that any case with a single band in the premutation range would be treated as apparent homozygosity, and would be subjected to secondary screening, which would also rule in or out mosaicism due to the presence of premutation plus full mutation alleles; such cases would not significantly affect the prevalence estimates. For samples from females that display a single band in the normal range (apparent homozygosity), the samples would be subjected to a secondary, CGG-directed primer-based PCR screening.

Example 5

The major difficulty encountered when screening for expanded alleles of the FMR1 gene is the ambiguity associated with a single band (apparent homozygosity) in females, which represent ~40-50% of female cases. In nearly all cases (~99.9%), the single band represents true homozygosity (i.e., two alleles differing by 0-2 repeats) However, the problem from the screening standpoint (standard PCR test) is that it is not possible to deduce which of the 40-50% of female cases with a single band have a non-amplifying full mutation (or a very high premutation).

To eliminate this ambiguity, the present invention uses a novel, PCR-based approach that involves a secondary PCR screen (of the apparent homozygous females) that combines the betaine PCR method with a chimeric primer that targets the CGG region itself. When used in combination with the standard primer c (Fu et al., 1991), the secondary PCR reaction produces an extended smear of amplified species only if an expanded allele is present (from the premutation to the full mutation range). Thus, the secondary screen returns a "yes or no" to the question of the presence of an expanded allele. The nature of the full mutation (or mosaics, which would automatically be flagged) can be characterized more fully in subsequent studies or clinical workup through more traditional methods (e.g., Southern blot); the purpose of the screen is to flag those cases.

This approach has been successfully performed using DNA collected from 15 normal females and 15 full mutation females, and using DNA isolated from blood spots from two normal females and two full mutation females. In all cases, PCR reactions consistently produce amplified products, which are visible as large smears on agarose gels, only in the full mutation females. The results were validated and confirmed by Southern blot analysis. Thus, the combination of the two PCR approaches allows detecting expanded FMR1 alleles in both females and males, regardless of the size, by PCR on blood spots. The methodology is therefore suitable for screening by collecting and using a small amount of DNA from blood spots, which never previously been successfully demonstrated or applied in screening fragile X samples, particularly for females. Two additional advantages of the inventive PCR approach are (i) that it lends itself to automation, and (ii) that no DNA primer or other DNA labeling is required.

Example 6

Female samples with a single band are subjected to a second round of screening, which utilizes the chimeric PCR approach. As for all other PCR reactions, the standard primer "c" is used; however, in place of the standard primer "f", the chimeric primer, 5'N24(CCG)n, is used. The N24 portion of the primer is mixed-sequence DNA that is approximately 50% AT. PCR amplification using "c" and the chimeric primer gives rise to an extended smear on the gel for expanded alleles. No smear has been detected in any case of a normal allele. The smear is generated by the amplification of expanded alleles even in the premutation range. However, premutation alleles can be separated by the betaine (primary) PCR screening method.

Example 7

FMRP ELISA

Methods:

Lymphocytes were separated from heparinized whole blood using Ficoll-Paque™ PLUS (Cat. No. 17-1440-02, GE Healthcare Bio-Sciences Corp., Piscataway, N.J.) and washed two times with phosphate buffered saline ("PBS", 137 mM NaCl, 2.7 mM KCl, 4.3 mM $Na_2HPO_4$, 1.4 mM $KH_2PO_4$) containing Complete (Cat. No. 11836153001, Roche) protease inhibitors by centrifugation at 1000×g. A pellet containing approximately $2 \times 10^6$ cells was resuspended in M-Per Mammalian Protein Extraction Reagent (No. 78503, Pierce, Rockford, Ill.) with 150 mM NaCl, Protease Inhibitor Cocktail Set III, 10 μg/ml antipain and 10 g/ml chymostatin, and rotated at 4° C. for two hours. Extracted proteins were spun at 14,000×g to pellet any non-solubilized cell debris, protein concentration of recovered supernatant was quantified using a colorimetric bicinchoninic acid assay (#23227, Pierce).

Affinity purified chicken IgY against the peptide sequence KDRNQKKEKPDSVD (SEQ ID NO.:3) was prepared by Aves Lab, Inc (Tigard, Oreg.). 100 ul (per well) of 2 ug/ml IgY diluted in PBS (137 mM NaCl, 2 mM KCl, 4.3 mM $Na_2HPO_4$ 1.4 mM $KH_2PO_4$) was incubated in Lumitrac 600 (Greiner) 96-well plates for 24-48 hours at 4° C. Unbound IgY was discarded, wells were blocked with 250 μl ELISA blocking buffer (2% hydrolyzed casein, 0.05% polyoxyethylene (20) sorbitan monolaurate, in PBS) at 20° C. for 12 hours. Wells were washed with 250 μl of PBS three times. Protein lysates and FMRP were diluted in PBS and added to wells, 100 μl sample volume per well, and incubated at 20° C. overnight. Wells were washed three times with PBS followed by three washes with PBS-T (PBS containing 0.05% polyoxyethylene (20) sorbitan monolaurate), 250 μl per well. Detecting antibody, mouse monoclonal anti-FMRP (MAB2160, Chemicon, Temecula, Calif.) was diluted to 1:10,000-1:20,000 in ELISA blocking buffer. 100 μl of detecting antibody was added to each well, and incubated for 8 hours at 20° C. Wells were washed with 250 μl per well of PBS-T five times. 100 μl per well of HRP conjugated donkey anti-mouse antibody (715-035-150, Jackson ImmunoResearch) diluted 1:5,000 in blocking buffer was added and incubated overnight at 20° C. Wells were washed with 250 μl PBS-T five times. 100 μl Lumigen PS-Atto (#PSA-100, Lumigen, Inc., Southfield, Mich.) luminescent substrate was added to each well and incubated for 5 minutes at room temperature. Luminescence accumulated over 2.5 sec was read for each well with a microplate luminometer (LMax, Molecular Devices, Sunnyvale, Calif.).

All publications and patent documents cited herein are incorporated by reference in their entirety for all purposes to the same extent as if each individual publication or patent document were individually denoted to be incorporated. Citation of various references in this document is not an admission that any particular reference is considered to be "prior art" to the invention.

What is claimed is:

1. A method for performing PCR to determine the presence or absence of an allele with expanded CGG repeats of the 5' untranslated region ("UTR") of the fragile X mental retardation 1 ("FMR1") gene in a biological sample from a subject, said method comprising amplifying the CGG repeat region of said 5' UTR region of the gene with a first primer and a second primer, wherein
   (a) said first primer is complementary to a portion of the 5' UTR region that is outside of the CGG repeat region; and,
   (b) said second primer is a chimeric primer comprising 3 to 30 consecutive repeats of CCG or 3 to 30 consecutive repeats of CGG at the 3' end of the second primer and a random nucleotide sequence at the 5' end of the second primer.

2. The method of claim 1, wherein said first primer has the sequence of SEQ ID NO.:1.

3. The method of claim 1, wherein the random nucleotide sequence is a sequence of 18-35 nucleotides.

4. The method of claim 3, wherein the random nucleotide sequence is a sequence of 21-30 nucleotides.

5. The method of claim 1, wherein said second primer consists of 4 to 8 repeats of CCG at the 3' end and a random nucleotide sequence of 18-35 nucleotides at the 5' end.

6. The method of claim 5, wherein said second primer consists of 4 repeats of CCG at the 3' end and a random nucleotide sequence of 18-35 nucleotides at the 5' end.

7. The method of claim 1, wherein said subject is a newborn.

8. The method of claim 7, wherein said biological sample is a blood spot.

9. The method of claim 1, wherein said subject is a female.

10. The method of claim 1, wherein said subject is a male.

11. The method of claim 3, wherein 30 to 70% of the nucleotides in the random nucleotide sequence are A or T nucleotides.

* * * * *

SEQUENCE LISTING

<160> NUMBER OF SEQ ID NOS: 15

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:PCR
      amplification primer "c" for fragile X mental
      retardation (FMR1) gene 5' untranslated region
      (UTR) flanking CGG repeat region, "c" primer of Fu

<400> SEQUENCE: 1
agccccgcac ttccaccacc agctcctcca                              30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:PCR
      amplification primer "f" for fragile X mental
      retardation (FMR1) gene 5' untranslated region
      (UTR) flanking CGG repeat region, "f" primer of Fu

<400> SEQUENCE: 2
gctcagctcc gtttcggttt cacttccggt                              30

```
<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:fragile X
      mental retardation protein (FMRP) peptide

<400> SEQUENCE: 3

Lys Asp Arg Asn Gln Lys Lys Glu Lys Pro Asp Ser Val Asp
 1               5                  10

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:"N24(CCG)-4"
      second chimeric primer

<400> SEQUENCE: 4
agcgtctact gtctcggcac ttgcccgccg ccgccg                          36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:"N24(CCG)-4"
      second chimeric primer

<400> SEQUENCE: 5
gacctgtatt gggtcacgtc agtcccgccg ccgccg                          36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:"N24(CCG)-4"
      second chimeric primer

<400> SEQUENCE: 6
agcgctatct cttccagagc tttcccgccg ccgccg                          36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:"N24(CCG)-4"
      second chimeric primer

<400> SEQUENCE: 7
gctcgctact gcttccggta ccgtccgccg ccgccg                          36

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:"N21(CCG)-4"
      second chimeric primer

<400> SEQUENCE: 8
gtctactgtc tcggcacttg cccgccgccg ccg                             33
```

```
<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:"N27(CCG)-4"
      second chimeric primer

<400> SEQUENCE: 9
attgctcgct actgcttccg gtaccgtccg ccgccgccg                          39

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:"N24(CCG)-3"
      second chimeric primer

<400> SEQUENCE: 10
agcgtctact gtctcggcac ttgcccgccg ccg                                33

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence:"N24(CCG)-6"
      second chimeric primer

<400> SEQUENCE: 11
agcgtctact gtctcggcac ttgcccgccg ccgccgccgc cg                      42

<210> SEQ ID NO 12
<211> LENGTH: 14040
<212> TYPE: DNA
<213> ORGANISM: Homo sapiens
<220> FEATURE:
<223> OTHER INFORMATION: fragile X mental retardation (FMR1) gene 5'
      untranslated region (UTR) upstream of start codon,
      CGG repeat region, start codon and portion of
      coding sequence
<220> FEATURE:
<221> NAME/KEY: repeat_region
<222> LOCATION: (13833)..(13962)
<223> OTHER INFORMATION: CGG repeat region
<220> FEATURE:
<221> NAME/KEY: misc_feature
<222> LOCATION: (13962)..(13964)
<223> OTHER INFORMATION: fragile X mental retardation (FMR1) gene start
      codon

<400> SEQUENCE: 12
atctctacac ttaagccata tcctctgctc catcaactag tttgccattt tgagtaatgg    60
gatgaagggt gcagcactca cagcaagctg cacgcccaac accatcatcc tcttcttcca  120
aaagaaatgc agttctgttt aggacagcaa ggtgtctggc tacaatcctc aggcttcctt  180
gtagctatgt gtggtcaggt aacatggtcc tagccaatga gatgtaagca gaaatctact  240
gaatgtagat ttctcaatgc agggagagca agtattttcc tgattattat tttttaaagg  300
agcagctggc atgtgccttt tgcactatgt tcttaaaccc tttttcctgc ataaaatgta  360
aactcatggt ctagagaagg agcagtcaac ttcccagcat gggaatttca aggaggatta  420
gtgggaagaa gaaggcgcca ccagactaca tcctgactgc ctgtctccag acttcttgtt  480
acataaaaag aaaaaatgaa ataaaataaa ataaacccttt tacttgttta agtcaatatt  540
tttcagattt aagtgatata tagtcaaatg taaccagatc aataaacaga gccacacttg  600
```

```
tgacatgtac tgacccagta agtgcagtag acagtgacag ttagtaacta ccttaaataa      660
tctctgagaa agatgtcagg agattagaga cagacaatat tccacatttc aatatttcaa      720
aagaaacata cagacctccc agcttaatca actcctggaa aaattctaaa cactattctc      780
tctaaacaga gtcacacttc tgaaagacat tgtttactgc ccttcaagta aagttcact       840
taactttggc agctcattga gcccaaatta atgcacaagc caaggtccat tgcagcttag      900
aaatatttct ctgcttcaat attaagagct ctcttaaagc actccttgat atgagaacaa      960
actagtcatg agtgctgctc ctcagaggca aaattctgtg tgggtttgtg gatgatgagg     1020
gcaatacatg caagggcta ggtccacaat tcagttttaa catcgttgaa aagacattta     1080
atgtgtgcag acactggttg agttatttac atagattatc tcatttgatg cccacacctc     1140
caatgagatg catgctttta ttatccccat tttatggata aggaaactga agcatagaga     1200
gatcaagtaa cttgcccaag aagactggtt aaagaagagc ctcattccta attcataaaa     1260
accttagaaa tctatccttt gtttggatct gataaccaaa atgagtgatt gtgctgtaag     1320
tctcaaaaca tcaaggttta ttgagccagc ttgagggtgc accaggaaaa atgtgagtca     1380
cagaagcatc tgtggctgtt ttttcccaa agaggtgaac aggaggttta gtatttacac     1440
attttcctta aaaatgaggg gtggtagtga gacaaataat tatatatttg tgagacttta     1500
gtggccagta aatccacact tacataaaac aaggtgaaca tttgaagaaa aagggaatgg     1560
agaaagcaaa tttcttgggg agaggtaaat aaatgattaa tctcattttg tctttgttct     1620
gtacctggga caataatcta gtagtctttt gaaagggctg gttctgtttt agcccttagg     1680
gaataaaacc tatgactgtt agcgagggag ggagtataat gaggcgtgtc caatctctca     1740
tcctgtcatg gccatgaatt cagctttcaa ggtttctctg cagttcccct ggccaagagg     1800
ggctctgttc attcagatga aggcttagaa ttttactttt atttctcaga tccatctgtg     1860
cagctcaggg aaactactaa ggctcccacc tccttaaaaa ttgccatttt ctcatgctac     1920
tggtcactga cgccttggtt taatgctttt tcctttttt tttttccttt cttaaacttt     1980
ttttagagac ggagtcttat tttgttgccc aagctgggt gcagtggcct gatcgtagct     2040
cactgtagcc tcaaactcct ggccagaagt gatcctccaa cctcagcctc taagtaact      2100
gagactatag gcatgcacca ccatgccagg ctaatttct tactttcttg tagagtggtg     2160
gggggtgcgg gggggaagtc tcactatgtt gtccaggctt ggctcaaact cctggcctca     2220
agcaatcttc tcaacttggc ctcccactgg gattacagga atgaaactgg cactttgagt     2280
ttacagagac aacatcccct ccacatttca tgtgacatat gtgcataaca aatggcaacc     2340
agcaaaactt tagtacttgg aatttcaaca atgttgagac tgatctttgc tttagttctt     2400
tgaatgggtg ggcctcaaca tgactcattg tagccaagtt gactcctgct cctcatagtt     2460
gttatctatt agtctggttg tttggttttg tacctcagat tccatatagg ttaggtgctc     2520
tatcagaaat gcatatggct gcaagttatt gaaaagccac tttagcaaca cctaatcaaa     2580
cagaggttta ttttctcac ataagtcgg tggtggctgg acacagtggc tcatgcctgt     2640
aatcccagca ctttgggagg ccaaggcgag tggatcgctt gagctcagga gttcgagacc     2700
agctgggca acatggtgaa accccggctc tacagaaaaa tacaaaatta gttgggtgtg     2760
gtgacgaaca cctgtagtcc cagctactca agaggctgag gtgggaggat agcttgcgat     2820
tctcttaacc gcagcctcaa ggtttcccta actttaggtg tcacatccat aaccaaggca     2880
ggcattacaa aagaagataa aacatcagcc aaatttgtcc ccttttctca aaaaagcaaa     2940
```

```
agcttttcta gaaacttccc tgtaaactta tgtttagatc acatttgcaa aaaaacaaaa    3000
atagtcacgt ggccactatg gtttcagggt tggctggaaa cttgcatatt taggttttcc    3060
actctctagg ttagaggcag gcaagagaaa ataaggctgg gcatggaagt caagttagcc    3120
aaaccagtga ctgtgacaga ttgcatgcta tttattctca atggataaag agaaaataat    3180
gtgattatct cataatgaaa tcaatactaa aatgaccttg agggtcaata cttctacttg    3240
taccggcttc ttggtgatgt ttgggctatg aatatcagtc ctgacactcg actccaagcc    3300
aagaaagaaa ttccaacgca aatgtctaat attgagctct gacatgtaca gagcttggaa    3360
actggcactc ctttcaacaa caacaaaaca ttgaacaaac agaaaagcaa tgacttatct    3420
tagaccaaga gatttaaggc cccagggcaa cctgccagca ccaaatttgg agcgataggt    3480
gaatacagag aatcagagca gaacttagat ttcctgaagc agcagccact ggagccaatt    3540
aggtaggaaa acttaagtgg tggttttggt gaattgcttg aggctgggtg tgggctagtt    3600
tgaaagttga aaattcctag gggacaaatc ggaggcaaag gctacacttt catggctttt    3660
gccttcagga accccaccag tttctgacag tatatatcag agaatttctg cttcctgttt    3720
cctgaaggag gagcaggaag caaccacttt gaaatatatt cagtatattc tttgtaacaa    3780
atgcttgccc tacgagggaa actacctttc cagaaccatt cctgacctag aagggatta    3840 ttagccagtg ctagtccttt ttagccttct tatctcatct aaagggagaa aaaaagctaa    3900
gaaataattc tgaagattac agcccaggaa ctcaactaaa aatctgaaat ttaatcataa    3960
aattatagaa catttccctt ccctaacacc atgccactgc atcaacagtg ctccagtata    4020
atagcaatag attacaatgg gagagctgag aaacccagac catttaagaa gaagttgata    4080
gggaaacgca aagacagcaa aggagacaaa acaaagata ctgaactaaa gcatctggca    4140
cctacagcta cagcaaacat taaacacccc aactcctaac tgattaacat aaaaagtcaa    4200
actaaaacct aattacctca gttcctatta cccaatacat tataccctgac tttcaacaaa    4260 aaattgcaag gaatgcagaa aggcaagaaa aaacacagtc tgtaaagata aagcgagcaa    4320
aggaaccaga cttaaatata acagtgattt tagaattatc agaaagtaaa tttaaaataa    4380
ttataattaa tatgtttaga gcactaatgg aaaaagtaga caacatgtaa gaacaaatgg    4440
gtaatgtaag cagagagaga gaaagaaaat ctccaagaaa gaattgtaaa aatgatagaa    4500 attttttaaaa aaacaactgt tacggaaaca caaatacctt tgatgggctc accagtagac    4560
tggaaacagc tgcgggaaga atcagcggaa agaaccaatg agattgaaga tatgttaata    4620
gaaacttctg ttaatcaagt ttatcctaaa gttgcctcct tacatattta agttcggcct    4680
aaaggttttt ctgcacatct tgaactataa caagtggagg tataaccaa ccatagcccg    4740 cacctgtgcc aatgactgaa ttttgactaa tcaaatgtag ccaactgttt gaaccctgtt    4800
taaataaagc taacaccaag ctgtaaccaa tccagttgtt tctgtacttg acttctgatt    4860
tctgtatgtc atttccttt tttgtctata atcttcttc catcacatgg ctgcactgga    4920
gtctctgtga atttgctgtg attttgggag ctgcccgatt caccaatcgt tcattgctca    4980
attaaactcc tttaaattta atttgcatga agtttttctt ttaacatttc ccaaactgaa    5040
atgcaaaaat tagatataaa aaaagaaaca aaatatccag gaactgtaga caattactaa    5100
aggtataata tgcttatatg agaatactag aagtaggaga gaaagaagca gaagaaatat    5160
atgaaataat aaaggctgat aattttccaa aatcagtgac agacaccaaa ccacacatcc    5220
aggaggctta aagacaccaa agcaggataa aatttaaaaa aaaaaagtc cacacctagt    5280 catattatgt tcaaatcaca gaaaactaaa acaaccagaa aacatgaaag aagctacaga    5340
```

```
agaggagaaa tttacctaag gagggacaaa gataagaatt acatcagaaa tctcattggc    5400
aaccatgcaa gaaagaagaa ggtagcgtga aatgtttaaa gtgttgaaag gataaaacta    5460
gaattctgga tacagtgaaa ttatccttca aaagcaaaga agaaatgctt tctcagacaa    5520
aggctgaatc tgtcaccagt agacctgcct tgaaataaat gttaaaagaa attttttcgga   5580 cagaaatgaa atgacatagg tcaaaaactg aaatctacat aaagaaaaga gctttcaaga   5640
aggaataaat gagcataaaa taaactcttt aatgttcctt aaccttaatt gatctaataa    5700
atataactat ttttcaaaa taattatgtt ttgggtgatt atagtatacg gataagtgaa      5760
gtgaataata gcaaaatttt aagggacata acggaggaat tgggaatact ctgtaataag    5820
gtacctgtac tacccatgaa gcactatagt gttatttgaa agtggactta attagatata    5880
aatatatact gcaaattcta gggaaactac tacatttta aaagtataat caatatctaa     5940
gatctctttt attagagaat aatataaaat gctcaattaa aaccagaaa ggcagtaaaa     6000 gaggaaaagt taaaaagaa accaagaaca agtgaaataa atggaaaaca gttaaaacat    6060
ggtatatatg aatctaacta tattattatc ataatcaatt taaatgtgaa tggtctaaat    6120
acataaatta aaaaatgaat aatgtcagaa tgaattattt taaaagaccc aattatgtat   6180
tgtctgcaag aagcccaatt taaacataaa gatataccta gattaaaagt aaagggatag    6240
aaaaagatat accatgctaa cactaatcaa aagaaagctg aagtagctat attaatttca   6300
gacaaagcaa acttcagggc aaggacatta tcaggaataa agaggggcat tacataccga   6360
taaaggtgtt aattctgcaa gaaaacataa aattccttat tgtatatcca tctagcaaca   6420
gtgtcaaaac atatgaggca aaagcagaca gagctgcaaa gagaaacaga caaatgcact   6480
gtcatatttg gagacttcaa cacctctctg tcagtaattt acagatatag ccaaaaacat   6540
cagtaaggat atagttgatg ctgaacatcc ttatcgatca acttgatcta atcaacatct    6600
atagacttta ttgtgtgtgt gtgtgtgtgt gtgtgtgtat gtgtgtgtca gtctcactct    6660
gtcactcagg cttggagtgc agtgggcaat ctctgctcac tgcaacctct gcctcccagc   6720
ttcaagtgac tctcatcatg cctcagcctc ctgagtagct gggattacag gcatgcacca   6780
ccacacccag ctaatttttt gcattttag tagagtcggc atttcactat gttggccagg    6840
ctggtctcga acttctggcc tcaagtgatc ctcccacctt agccttgcaa agtactggga   6900
ttacaggcat cagccactgt gcctggcctg atatttatag actatttgat ccaacagaga   6960
cagaatacac atttctttca tgttcacatg gaacattaat caagatagac cacattctgt   7020
ttcataaaat tcaccttaaa aattaaaaaa acagaaatca aacaagatat tttcacagat   7080
tacaataaaa ttaaactaga tattttaga aacctagaaa tatgctaggc aatgccctca    7140
aatatttgga gattaaacaa cacacttcta ataatatat ggatcaaaga agatgtttca    7200
agagatatta aaaatatttt gaactaaatg aaaaaataaa ctttttaaaa tttatgggat   7260
gcagcaaaag cagtgatgag agggaaattt atatatcagc aatgaacaat tggaatttga   7320
aattaaaaac ataccattca aaccagcact gaaaacaaa atatttaggt ataaatctaa    7380
taaaatatgt acagaatcta gttcaacacc ttatgaaaga aatgaaaaat ctaaataaat   7440
tgagaaatat cccatgttca taaatagcaa gactaatgtt gttaaactgt cacttcttcc   7500
ctacttgatc tatagattca atgctgtctg aatcaaaatc ctagcaagtt attttgtgaa   7560
tattgacaaa ctgactgtaa agtctatatg gaaagacaga agatccagaa taggcagtat   7620
aatattgagg aagaacaaag ttggaagaca gacactatct tacttcaaag cttattacaa   7680
```

```
agttacagta gtcaagacag tagggtattg atgaaagaaa agagaaatac tgttgttcct   7740
cagtatcatg gggggaactg gttgcaggat gtctgaggat accaaaacct gtggattctc   7800
aagtttctta tataatacga cgtagtgttt gcatataacc tatgcacatc ctcctcctgt   7860
atactttaaa tcatctctag attatatata atacctaaca caatgtaaat gctatgtaac   7920
agttatactt tattgatttt ttatttgtat tattttatt gttatattgt tattttagg    7980 ggattttctt tttgagactg agtcttgcac tgtcgtcagg gctggagtgc agtggtgcgg   8040
tcttggctca gtgcaacctc tgcctcctgg gttcaagtga ttctcctgcc tcaccttcct   8100
gagcagcttg gattacaggt gcccgccacc atgctcagct aatttttgt attttagta    8160 gagacggggc ttcactatgt tggccaggcc ggtctcgaac tcctgacctg ataatccccc   8220
caccttggcc tcccaaagta ccaaaattac aggcatgagc caccctcct ggccatttt    8280 aggggatttt taaagaatat ttttgatctg tcattggttg aatctgttga tgcagaaccc   8340
atggatacag agggccaact gtagataaat ggaacaaaat aaagatgcca gaattagatc   8400
catacaaata cagtcaactg atcattgaca aaggagcaaa taattcaatg gagaaacaat   8460
ggtcttttca acaacggtg ctggaataac tggacattca tatgcaaaaa acaatctaga   8520
cacagacctt atatctttca caaaaattta ctcaaaatgg atcatagacc taaatgcaaa   8580
acacaaaact gtaaacttc tggaagataa cataggagaa atctaggtg aacttgtgtt   8640 tggtgatgac tttttgggta caatgctaaa agcacgatcc ctgaaaaaaa ctgaacagtc   8700 gaaattttt cattacaaat gtctgctcaa tgaaagacat tgttaaatga atgaaaagac   8760
aagccactgt ctgggagaaa atatctgcaa aatacataat ctgataaagg gctgatatct   8820
aaaatatata aagaacactg aaaaatcatc aataaaaaaa acccaatggg taacagatct   8880
gagcagacac cttatcaaag aagatacata cgtgacaaac aagcataaga tgcccaatgc   8940
catatgtcat taggaaattg caaactaaaa caataagatt ctactatgca cctattaaaa   9000
tacccaaaat tcaaaatact ggcaacacca aatgttggca aggatgtgga gtaacaggaa   9060
gtctcactca ttgctggtga aaatgcaaac tgttacagcc actttggaag atcatctggt   9120 aattttgat aaagcaaaac atagtcttac catatgatcc agcaatcatg ctccttggta   9180
tttacctaaa tgagttgaaa acttatgtcc atacaaaaat ctgtacaaga agtttacag   9240 gagccttatt cataatttta aaagactgaa agcaaccaag atgtctttca ataaataaat   9300
ggataaacaa accatggtat atacatacag tggaatactg tgcacaataa aagaaaataa   9360
actatcaagc catgaaaaga cacagaggaa tgttaaatgt atattgctaa gtaaaaaaaa   9420
aaaagcagta tgaaaagact acatactata tgattccaac tctatgacat tacggaaaag   9480
gcaaaattct gcagaaagta aaaacatcag tgattgccaa gggttggttg caggtagacc   9540
agatgaatag gtggaacaca aggaattttt taatgcagtg taattgttct gctgacactg   9600
taatggtgga tatgttatgc ttttttcaaa acccacagag ctatgcaaca caagagtga    9660 atcttaatgt aaactataga ctttagttag taataatgca tcagttgtaa taaatgtaca   9720
atgcgaatgc aagatgttaa taacaggagg aactgtaggg gaggagggag attaggaagt   9780
acatagaaac tctctccact atctgcttaa ttttccata aatgtaaaac tgttctaaaa    9840
aataaagcca attaattatt cttttctaa tatctcattt gaatgagagg tcatggttaa    9900
aggaaattgt cagagaaagt gtcaagaaag aagtgtgact ttagctgggt cctgaagggt   9960
acataagatt tgagagtcgg aaagggcaga aggcatttca gctgggtttg agccatggaa  10020
aagactcaga gggctcaaat tgcgaaggag caggaaatag cacagaataa atcaatgcaa  10080
```

```
agacaacagg cagcaattta atggaaacca agggccaagg cagggctaga aacactgaag   10140
catcattcca atatcagata aatataggca tgagagctga ctcaacctcg gccgggtcct   10200
caacacatat tcgttcattc atgtaatatt tagtaaacat tcactatgtt ccagacactg   10260
tggtaggcac tggggacaag cagtgaataa acaaatgga aatctttgtt ctcactgagc   10320
ttacactcta gtgaggggag agagacagaa cctgtctgct attttcaaga aacaacaaag   10380
aaaacattat ggctggaatg agaaacaatg ccttttcaa taaacagtgc tggaataact   10440
ggacattcat atgcaaaaaa taatctagat acagaccta tatcttttga aaaaattta    10500 ctcaaaatgg atcatagacc taaatgcaaa acacaaaact gtaaaacttc tgaaagataa   10560
cataggagaa atctaggtg aactagatag atttcatgca ctggaatgaa gtgaaggggg    10620
aaagtagaag gtgagatagc ggagataaca gaagtcagag tatatagggc actgaagcca   10680
gaataaataa tgactctggc ttttactctg agagatgtag ggagtcactg ggggattgtg   10740
agtggcagag tgacttgatt gacacctcaa cagggtcatt ctgtcttctg tgctgagaac   10800
tgtcagagag ggtacaacag tggacagtga ctgcagggat accagcgaag aagttgctgc   10860
cataatgcag gtaagagaat ggaagcttgg actatggttt tagctgagca aatgatcaga   10920
aacagagtct ggattctaca atgatttgct gatggatctg atgtgtgaaa gagggtcaaa   10980
atgtctcagt tttaggcttg agcaacgaac tggaaggcag gagctgcctg taacgagaga   11040
caggagagaa agagagagag agagagagga ctttggaaga gcaggctcat gatcaggcct   11100
gagctcagtg tctgaattca ggtaagctat cttgaaaggg gaaatatcaa aagctagaga   11160
tcagagtaag gctgagactc agagtcaagt ggggaagact aagttgcagt atgtactggc   11220
agtgaagata agtatttatt cattcattga acataccttg aaatcaacca cttttaatgt   11280
gccagggaca caaagataga aaagacattt gccctgtctg gaaggtacta ataatccaat   11340
aaggaaaaca gaaatataaa taaattattc tagtacacta accatcatag tagaggtatt   11400
caacatttgt tgagtctctg ctatatgcca agcagtgtaa tgaggaagca gagggtatgc   11460
acaaagttct acaagagcac aaaataagtt ctggcaaagg tttgtaaaga cattcacaag   11520
ggttttcacc acagtatgac ttcagggagt tggcagtaac ctagatgccc gatcagtagg   11580
gatatgtatg aataaaattt ctggcatact cggtagcaaa ctaggtgtac acacagcaat   11640
gtgggtatag ctcaaaaaca gactgttgag taaaacagtg ggaaatagag atttacagtc   11700
caataccatc tctgtaaatg caagaggcat aaacaaaaca ttatctgtgt taaattatca   11760
aggatctcta tcgaacatat tgcagcttgt gtctagaaga atgagagtgg ggatcgagaa   11820
agatgaggaa aaaataatat aaacactata aaataatgta aacaaggacc ctgtagggac   11880
tgatatgaca atgtgctgaa aattgaggag caaagttaac tctctgtacc tgagataaaa   11940
taactagcta ataggaatcc agctgaaaac cttaaggtgc agggcctcta tggggcccag   12000
gaaggatgtg tagagacatg aacggatgaa agtgcatcac aggttcaggg aacaacacag   12060
gttgagtgtg gcttgtagta aaaatggttg tgaagagttg acatattttt aagccctggg   12120
taaattgaac aacagcttac acttggaggg gtataatcat tctaatcaat gtgtcccctt   12180
ttactataat acattggagt tgcagctaat gctctgctcc cattcagcct atgatgagat   12240 tctcttttcag ccctattggg ttcttggcct catgtgacta ctccaaagac cctagtccaa   12300
aaggtctttc ctgtttgcta tggccttgag gaatgtggcc ctagatccac cgctttaaag   12360
ctggagttcc accagcagca acatcctctc attctggggc acctgcctgg ggcaggtcat   12420
```

```
cctgcctctg ccaactcagt gctattagtt aactctcacc tgccatattc cagctggaat    12480
catctcccct tctccacccc agactaggtc atgttccgcc atcatggaag cgcctattct    12540 tcataccoct tatcacagct gcaactactc atttacttgt ctgacaattt gatttatgtc    12600
cacctacttt gctaggtact aagttcaatg ctggcagtcg tttcttcttt tttttttcttt    12660 tctgttttgc tcaccgattt ctcgttagca cttagcacag tgtctggcac acgatagatg    12720
ctccgtcaac ttctcagttg gataccagca tcccgaaggg aacatggatt aaggcagcta    12780
taagcacggt gtaaaaacag gaataagaaa aagttgaggt ttgtttcaca gtggaatgta    12840
aagggttgca aggaggtgca tcggcccctg tggacaggac gcatgactgc tacacacgtg    12900
ttcaccccac cctctggcac agggtgcaca tacagtaggg gcagaaatga acctcaagtg    12960
cttaacacaa ttttttaaaaa atatatagtc aagtgaaagt atgaaaatga gttgaggaaa    13020
ggcgagtacg tgggtcaaag ctgggtctga ggaaaggctc acattttgag atcccgactc    13080
aatccatgtc ccttaaaggg cacagggtgt ctccacaggg ccgcccaaaa tctggtgaga    13140
gagggcgtag acgcctcacc ttctgcctct acgggtcaca aaagcctggg tcaccctggt    13200
tgccactgtt cctagttcaa agtcttcttc tgtctaatcc ttcaccccta ttctcgcctt    13260
ccactccacc tcccgctcag tcagactgcg ctactttgaa ccggaccaaa ccaaaccaaa    13320
ccaaaccaaa ccaaaccaga ccagacaccc cctcccgcgg aatcccagag aggccgaact    13380
gggataaccg gatgcatttg atttcccacg ccactgagtg cacctctgca gaaatgggcg    13440
ttctggccct cgcgaggcag tgcgacctgt caccgccctt cagccttccc gccctccacc    13500
aagcccgcgc acgcccggcc cgcgcgtctg tctttcgacc cggcaccccg gccggttccc    13560
agcagcgcgc atgcgcgcgc tcccaggcca cttgaagaga gagggcgggg ccgaggggct    13620
gagcccgcgg ggggagggaa cagcgttgat cacgtgacgt ggtttcagtg tttacacccg    13680
cagcgggccg ggggttcggc ctcagtcagg cgctcagctc cgtttcggtt tcacttccgg    13740
tggagggccg cctctgagcg ggcggcgggc cgacggcgag cgcgggcggc ggcggtgacg    13800
gaggcgccgc tgccagggggg cgtgcggcag cgcggcggcg gcggcggcgg cggcggcggc    13860
ggaggcggcg gcggcggcgg cggcggcggc ggctgggcct cgagcgcccg cagcccacct    13920
ctcgggggcg ggctcccggc gctagcaggg ctgaagagaa gatggaggag ctggtggtgg    13980
aagtgcgggg ctccaatggc gctttctaca aggtacttgg ctctagggca ggccccatct    14040
```

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence:3' (CCG)-4
      block for targeting "N24(CCG)-4" second chimeric
      primer

<400> SEQUENCE: 13
ccgccgccgc cg                                                          12

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:"N24(CCG)-4"
      second chimeric primer including 3' (CCG)-4 block
      for targeting and 5' random N24 block for
      amplification
<220> FEATURE:

```
<221> NAME/KEY: modified_base
<222> LOCATION: (1)..(24)
<223> OTHER INFORMATION: n = g, a, c or t, 5' random N24 block

<400> SEQUENCE: 14
nnnnnnnnnn nnnnnnnnnn nnnnccgccg ccgccg                           36

<210> SEQ ID NO 15
<211> LENGTH: 360
<212> TYPE: DNA
<213> ORGANISM: Homo sapiens
<220> FEATURE:
<223> OTHER INFORMATION: fragile X mental retardation (FMR1) gene 5'
      untranslated region (UTR) immediately upstream of
      start codon, CGG repeat region, start codon and
      beginning of coding sequence
<220> FEATURE:
<221> NAME/KEY: repeat_region
<222> LOCATION: (153)..(212)
<223> OTHER INFORMATION: CGG repeat region
<220> FEATURE:
<221> NAME/KEY: misc_feature
<222> LOCATION: (282)..(284)
<223> OTHER INFORMATION: fragile X mental retardation (FMR1) gene start
      codon

<400> SEQUENCE: 15
cagcgggccg ggggttcggc ctcagtcagg cgctcagctc cgtttcggtt tcacttccgg     60
tggagggccg cctctgagcg ggcggcgggc cgacggcgag cgcgggcggc ggcggtgacg    120
gaggcgccgc tgccaggggg cgtgcggcag cgcggcggcg gcggcggcgg cggcggcggc    180
ggaggcggcg gcggcggcgg cggcggcggc ggctgggcct cgagcgcccg cagcccacct    240
ctcgggggcg ggctcccggc gctagcaggg ctgaagagaa gatggaggag ctggtggtgg    300
aagtgcgggg ctccaatggc gctttctaca aggtacttgg ctctagggca ggccccatct    360
```